United States Patent [19]
Hörlein et al.

[11] 3,948,945
[45] Apr. 6, 1976

[54] 5-HOMOTHIOCHROMANYL-(DI)-PHOSPHORIC (-PHOSPHONIC) ACID ESTERS

[75] Inventors: Gerhard Hörlein, Frankfurt am Main; Gerhard Salbeck, Kelkheim, Taunus; Ludwig Emmel, Bergen-Enkheim; Werner Bonin, Kelkheim, Taunus, all of Germany

[73] Assignee: Hoechst Aktiengesellschaft, Frankfurt am Main, Germany

[22] Filed: Aug. 12, 1974

[21] Appl. No.: 496,891

[30] Foreign Application Priority Data
Aug. 14, 1973  Germany............................ 2341022

[52] U.S. Cl. ............................ 260/327 B; 424/275
[51] Int. Cl.² ........................................ C07D 337/08
[58] Field of Search................ 260/327 B, 327 TH

[56] References Cited
UNITED STATES PATENTS 3,590,052  6/1971  Barker.......................... 260/327 TH
3,714,190  1/1973  Boissier et al................ 260/327 TH
3,816,456  6/1974  Horlein et al. ............... 260/327 TH Primary Examiner—Henry R. Jiles
Assistant Examiner—C. M. S. Jaisle
Attorney, Agent, or Firm—Curtis, Morris & Safford

[57] ABSTRACT

The invention provides 5-homothiochromanyl-(di)-phosphoric (-phosphonic) acid esters of the formula

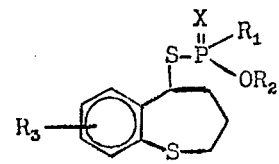

where
$R_1$ is $(C_1-C_4)$alkyl, $(C_1-C_4)$ alkoxy,
$R_2$ is $(C_1-C_4)$alkyl,
$R_3$ is hydrogen, $(C_1-C_4)$alkyl or halogen, and
X is oxygen or sulfur.

8 Claims, No Drawings

5-HOMOTHIOCHROMANYL-(DI)-PHOSPHORIC (-PHOSPHONIC) ACID ESTERS

The present invention provides 5-homothiochromanyl-(di)-thio-phosphoric (-phosphonic) acid esters of the formula

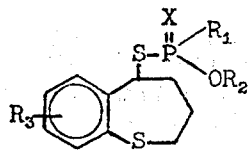
           I where
$R_1$ is $(C_1-C_4)$alkyl, $(C_1-C_4)$ alkoxy,
$R_2$ is $(C_1-C_4)$alkyl,
$R_3$ is hydrogen, $(C_1-C_4)$alkyl or halogen, and
X is oxygen or sulfur.

The compounds of the invention are obtained by reacting homothiochromanyl compounds of the formula

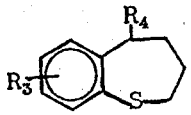
           II with phosphorus compounds of the formula

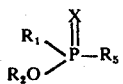
           III in which formulae one of the radicals $R_4$ and $R_5$ is halogen, especially chlorine or bromine, and the other the SY group (Y being hydrogen or a metal cation); the reaction being carried out optionally in the presence of an acid binding agent.

a. The phosphorus compounds of formula III ($R_5$ = SY) react without difficulty with halogenated homothiochromanes of formula II ($R_4$ = Hal); temperatures of from 0° to 120°C, preferably from 10° to 80°C, being advantageously used for this reaction. It is recommended to carry out the process of the invention in the presence of an inert solvent or diluent. Suitable solvents include aliphatic ketones such as acetone or methylethylketone; alcanols such as methanol, ethanol or isopropanol; esters such as acetic acid ethyl ester; nitriles; N-alkylated acid amides such as dimethyl formamide; ethers such as dioxan, glycol dimethyl ether or tetra-hydrofuran; chlorinated hydrocarbons such as chloroform or carbon tetrachloride; water; or mixtures of such solvents.

During the reaction the halogen atom of the homothiochromanyl compound has to be split off. In order to achieve this, the reaction is carried out either with addition of an acid binding agent, or using the salts, especially the alcali metal or ammonium salts, of the phosphorus compounds. As acid binding agents, the alkali metal hydroxides or carbonates are preferred, but tertiary nitrogen bases such as pyridine or triethylamine may also be used.

The 5-halo-homothiochromanes of formula II and their preparation are either described in the linterature (Collect. czechoslov. chem. Commun. 33 (12) 4315 (1968)), or they may be prepared in analogous manner according to known processes.

The compounds of formula III in which $R_5$ is SY are known and may be easily obtained according to known methods.

b. It is also possible to react 5-mercapto-homothiochromanes (formula II; $R_4$ = SY) with halo-phosphorus compounds (formula III; $R_5$ = Hal); in the case of $R_4$ being SH, the reaction is carried out also in the presence of an acid-binding agent. Generally, about stoichiometric amounts of the reactants are used; however, an excess of from 5 to 10% of formula III compound may be advantageous.

The reaction according to (b) is preferably also carried out in the presence of an inert solvent as cited above. The reaction temperatures may vary within a wide range; preferably, temperatures from 50° to 120°C are used. As acid binding agents the same as above may be used.

The mercapto-homothiochromanes of formula III may be obtained for example from the 5-halo-homothiochromanes according to known methods. The halophosphorus compounds of formula III are known and easily obtainable according to known methods.

Compounds obtainable by the above processes include the following:

5-homothiochromanyl-(di)-thio-phosphoric acid dimethyl ester, -diethyl ester, -di-isopropyl ester, 7-methyl-5-homothiochromanyl-(di)-thio-phosphoric acid dimethyl ester, -diethyl ester, -dibutyl ester, 7-ethyl-5-homothiochromanyl-(di)-thio-phosphoric acid dimethyl ester, -diethyl ester, -dibutyl ester, 7-n-butyl-5-homothiochromanyl-(d)-thio-phosphoric acid dimethyl ester, -diethyl ester, -di-n-propyl ester, 7-fluoro-5-homothiochromanyl-(di)-thio-phosphoric acid dimethyl ester, -diethyl ester, -di-n-propyl ester, 7-chloro-5-5-homothiochromanyl-(di)-thio-phosphroic acid dimethyl ester, -diethyl ester, -dibutyl ester, 7-bromo-5-homothiochromanyl-(di)-thio-phosphoric acid dimethylester, -diethyl ester, -di-n-propyl ester, 8-methyl-5-homothiochromanyl-(di)-thio-phosphoric acid dimethyl ester, -diethyl ester, -dibutyl ester, 8-ethyl-5-homothiochromanyl-(di)-thio-phosphoric acid dimethyl ester, -diethyl ester, -dibutyl ester, 8-n-propyl-5-homothiochromanyl-(di)-thio-phosphoric acid dimethyl ester, -diethyl ester, -di-n-propyl ester, 8-fluoro-5-homothiochromanyl-(di)-thio-phosphoric acid dimethyl ester, -diethyl ester, -di-n-propyl ester, 8-chloro-5-homothiochromanyl-(di)-thio-phosphoric acid dimethyl ester, -diethyl ester, -dibutyl ester, 8-bromo-5-homothiochromanyl-(di)-thio-phosphoric acid dimethyl ester, -diethyl ester, -di-n-propyl ester, 9-methyl-5-homothiochromanyl-(di)-thio-phosphoric acid dimethyl ester, -diethyl ester, -dibutyl ester, 9-ethyl-5-homothiochromanyl-(di)-thio-phosphoric acid dimethyl ester, -diethyl ester, -dibutyl ester, 9-butyl-5-homothiochromanyl-(di)-thio-phosphoric acid dimethyl ester, -diethyl ester, -di-n-propyl ester, 9-fluoro-5-homothiochromanyl-(di)-thio-phosphoric acid dimethyl ester, -diethyl ester, -d-n-propyl ester, 9-chloro-5-homothiochromanyl-(di)-thio-phosphoric acid dimethyl ester, -diethyl ester, -dibutyl ester, 9-bromo-5-homothiochromanyl-(di)-thio-phosphoric acid dimethyl ester, -diethyl ester, -di-n-propyl ester, 5-homothiochromanyl-(di)-thio-methane-phosphonic acid methyl ester, -ethyl ester, -butyl ester, 7-methyl-5-homothiochromanyl-(di)-thio-methane-phosphonic acid methyl ester, -ethyl ester, -butyl ester, 7-ethyl-5-homothiochromanyl-(di)-thio-methane-phosphonic acid methyl ester, -ethyl ester, -butyl ester, 7-n-butyl-5-homothiochromanyl-(di)-thio-methane-phosphonic acid methyl ester, -ethyl ester, -n-propyl ester, 7-fluoro-5-homothiochromanyl-(di)-thio-methane-phosphonic acid methyl ester, -ethyl ester, -n-propyl ester, 7-chloro-5-homothiochromanyl-(di)-thio-methane-phosphonic acid methyl ester, -ethyl ester, -butyl ester, 7-bromo-5-homothiochromanyl-(di)-thio-methane-phosphonic acid methyl ester, -ethyl ester, -n-propyl ester, 8-methyl-5-homothiochromanyl-(di)-thio-methane-phosphonic acid methyl ester, -ethyl ester, -butyl ester, 8-methyl-5-homothiochromanyl-(di)-thio-methane-phosphonic acid methyl ester, -ethyl ester, -butyl ester, 8-n-propyl-5-homothiochromanyl-(di)-thio-methane-phosphonic acid methyl ester, -ethyl ester, -n-propyl ester, 8-fluoro-5-homothiochromanyl-(di)-thio-methane-phosphonic acid methyl ester, -ethyl ester, -n-propyl ester, 8-chloro-5-homothiochromanyl-(di)-thio-methane-phosphonic acid methyl ester, -ethyl ester, -butyl ester, 8-bromo-5-homothiochromanyl-(di)-thio-methane-phosphonic acid methyl ester, -ethyl ester, -n-propyl ester, 9-methyl-5-homothiochromanyl-(di)-thio-methane-phosphonic acid methyl ester, -ethyl ester, -butyl ester, 9-ethyl-5-homothiochromanyl-(di)-thio-methane-phosphonic acid methyl ester, -ethyl ester, -butyl ester, 9-butyl-5-homothiochromanyl-(di)-thio-methane-phosphonic acid methyl ester, -ethyl ester, -n-propyl ester, 9-fluoro-5-homothiochromanyl-(di)-thio-methane-phosphonic acid methyl ester, -ethyl ester, -n-propyl ester, 9-chloro-5-homothiochromanyl-(di)-thio-methane-phosphonic acid methyl ester, -ethyl ester, -butyl ester, 9-bromo-5-homothiochromanyl-(di)-thio-methane-phosphonic acid methyl ester, -ethyl ester, -n-propyl ester, 7-methyl-5-homothiochromanyl-(di)-thio-ethane-phosphonic acid methyl ester, -ethyl ester, -butyl ester, 7-ethyl-5-homothiochromanyl-(di)-thio-ethane-phosphonic acid methyl ester, -ethyl ester, -butyl ester, 7-n-butyl-5-homothiochromanyl-(di)-thio-ethane-phosphonic acid methyl ester, -ethyl ester, -n-propyl ester, 7-fluoro-5-homothiochromanyl-(di)-thio-ethane-phonsphonic acid methyl ester, -ethyl ester, -n-propyl ester, 7-chloro-5-homothiochromanyl-(di)-thio-ethane-phosphonic acid methyl ester, -ethyl ester, -butyl ester, 7-bromo-5-homothiochromanyl-(di)-thio-ethane-phosphonic acid methyl ester, -ethyl ester, -n-propyl ester, 8-methyl-5-homothiochromanyl-(di)-thio-ethane-phosphonic acid methyl ester, -ethyl ester, -butyl ester, 8-ethyl-5-homothiochromanyl-(di)-thio-ethane-phosphonic acid methyl ester, -ethyl ester, -butyl ester, 8-n-propyl-5-homothiochromanyl-(di)-thio-ethane-phosphonic acid methyl ester, -ethyl ester, -n-propyl ester, 8-fluoro-5-homothiochromanyl-(di)-thio-ethane-phosphonic acid methyl ester, -ethyl ester, -n-propyl ester, 8-chloro-5-homothiochromanyl-(di)-thio-ethane-phosphonic acid methyl ester, -ethyl ester, -butyl ester, 8-bromo-5-homothiochromanyl-(di)-thio-ethane-phosphonic acid methyl ester, -ethyl ester, -n-propyl ester, 9-methyl-5-homothiochromanyl-(di)-thio-ethane-phosphonic acid methyl ester, -ethyl ester, -butyl ester, 9-ethyl-5-homothiochromanyl-(di)-thio-ethane-phosphonic acid methyl ester, -ethyl ester, -butyl ester, 9-butyl-5-homothiochromanyl-(di)-thio-ethane-phosphonic acid methyl ester, -ethyl ester, -n-propyl ester, 9-fluoro-5-homothiochromanyl-(di)-thio-ethane-phosphonic acid methyl ester, -ethyl ester, -n-propyl ester, 9-chloro-5-homothiochromanyl-(di)-thio-ethane-phosphonic acid methyl ester, -ethyl ester, -butyl ester, 9-bromo-5-homothiochromanyl-(di)-thio-ethane-phosphonic acid methyl ester, -ethyl ester, -n-propyl ester, 5-homothiochromanyl-(di)-thio-ethane-phosphonic acid methyl ester, -ethyl ester, -butyl ester, 5-homothiochromanyl-(di)-thio-butane-phosphonic acid methyl ester, -ethyl ester, -butyl ester, 7-methyl-5-homothiochromanyl-(di)-thio-butane-phosphonic acid methyl ester, -ethyl ester, -butyl ester, 7-ethyl-5-homothiochromanyl-(di)-thio-butane-phosphonic acid methyl ester, -ethyl ester, -butyl ester, 7-n-butyl-5-homothiochromanyl-(di)-thio-butane-phosphonic acid methyl ester, -ethyl ester, -n-propyl ester, 7-fluoro-5-homothiochromanyl-(di)-thio-butane-phosphonic acid methyl ester, -ethyl ester, -n-propyl ester, 7-chloro-5-homothiochromanyl-(di)-thio-butane-phosphonic acid methyl ester, -ethyl ester, -butyl ester, 7-bromo-5-homothiochromanyl-(di)-thio-butane-phosphonic acid methyl ester, -ethyl ester, -n-propyl ester, 8-methyl-5-homothiochromanyl-(di)-thio-butane-phosphonic acid methyl ester, -ethyl ester, -butyl ester, 8-ethyl-5-homothiochromanyl-(di)-thio-butane-phosphonic acid methyl ester, -ethyl ester, -butyl ester, 8-n-propyl-5-homothiochromanyl-(di)-thio-butane-phosphonic acid methyl ester, -ethyl ester, -n-propyl ester, 8-fluoro-5-homothiochromanyl-(di)-thio-butane-phosphonic acid methyl ester, -ethyl ester, -n-propyl ester, 8-chloro-5-homothiochromanyl-(di)-thio-butane-phosphonic acid methyl ester, -ethyl ester, -butyl ester, 8-bromo-5-homothiochromanyl-(di)-thio-butane-phosphonic acid methyl ester, -ethyl ester, -n-propyl ester, 9-methyl-5-homothiochromanyl-(di)-thio-butane-phosphonic acid methyl ester, -ethyl ester, -butyl ester,
9-ethyl-5-homothiochromanyl-(di)-thio-butane-phosphonic acid methyl ester, -ethyl ester, -butyl ester,
9-butyl-5-homothiochromanyl-(di)-thio-butane-phosphonic acid methyl ester, -ethyl ester, -n-propyl ester,
9-fluoro-5-homothiochromanyl-(di)-thio-butane-phosphonic acid methyl ester, -ethyl ester, -n-propyl ester,
9-chloro-5-homothiochromanyl-(di)-thio-butane-phosphonic acid methyl ester, -ethyl ester, -butyl ester,
9-bromo-5-homothiochromanyl-(di)-thio-butane-phosphonic acid methyl ester, -ethyl ester, -n-propyl ester.

Preferred compounds of formula I are those where $R_1$ and/or $R_2$ contain 1 or 2 carbon atoms and $R_3$ is in 7-, 8- or 9-position (to the cylic S atom), especially in 7-position and represents halogen, preferably fluorine, chlorine or bromine, especially chlorine.

The compounds of formula I are suitable for the destruction of numerous pests in their various development stages of different crop plants. They combine a good plant tolerability with valuable insecticidal, acaricidal and nematocidal properties. Thus, different spider mite species, for example the European red mite (*Metatetranychus ulmi*), or mites like *Panonychus citri* or *Tetranychus urticae*, among these also strains resistant to phosphoric esters, can be controlled with very good results.

In addition, the invention compounds destroy numerous biting and sucking insects noxious to crop plants, for example beetles, such as the Mexican bean beetle (*Epilachna varivestis*), the Colorado beetle (*Leptinotarsa decemlineata*), the flower beetle (*Epicometis hirta*), the flea beetle (*Phyllotreta spp.*), the strawberry borer (*Coenorrhinus germanicus*), or the boll weevil (*Anthonomus grandis*); butterflies and their larvae, such as the Egyptian and the Old World boll worm (*Earias insulana* and *Heliothis armigera*); leaf rollers, especially the codling moth (*Carpocapsa pomonella*), the green oak roller (*Tortrix viridana*), the tortix moth (*Capua recticulana*), the corn borer (*Ostrinia nubilalis*) or the winter moth (*Cheimatobia brumata*); aphids, such as the bean aphid (*Doralis fabae*), the green peach aphid (*Myzodes persicae*), the cotton aphid (*Aphis gossypii*); or bugs, such as milkweed bugs and cotton strainers (*Oncopeltus fasciatus* and *Dysdercus spp.*, especially *fasciatus*).

The compounds of the present invention are also suitable for combating ectoparasites living on productive livestock. Thus, mallophaga, lice (*Anoplura*), fleas (*Aphaniptera*), mites and ticks (*Acarina*, such as ixodides (*Ixodidae*), argasides (*Argasidae*), dermanyssides (*Dermanyssidae*); sarcoptides (*Sarcoptidae*), as well as those resistant to phosphoric esters, are destroyed.

Additionally, the compounds have a proved systemic action in animals. They are therefore especially suitable for combating parasites the development of which partially takes place in the animal body and which therefore cannot be attained by external treatment.

A number of the invention compounds have a very low toxicity to fish, so that they may be used, for example, for combating infection-carrying mosquitoes (yellow fever mosquitoes, anopheles) in their larval stage.

The compounds are furthermore suitable for combating different nematode species noxious to plants.

The phosphorus compounds of formula I may be formulated in usual admixture with solid or liquid inert carrier substances, adhesives, wetting and dispersing agents, or grinding auxiliaries in the form of wettable powders, emulsions, suspensions, dusting powders, granules, fly-bands, and products for spreading and washing. They may be mixed with other insecticides, fungicides, nematocides and herebicides.

As carrier material, mineral substances, for example aluminium silicates, argillaceous earths, kaolin, chalks, siliceous chalks, talcum, kieselguhr or hydrated silicic acids can be used, or preparations of these mineral substances with special additives, for example chalk with sodium stearate. As carrier material for liquid preparations, all usual and suitable organic solvents may be employed, for example toluene, xylene, diacetone alcohol, isophorone, gasolines, paraffin oils, dioxan, dimethyl formamide, dimethyl sulfoxide, ethyl acetate, butyl acetate, tetrahydrofuran, chlorobenzene and others.

Suitable adhesives are glue-like cellulose products or polyvinyl alcohols.

As wetting agents, all suitable emulsifiers may be used, for example ethoxylated alkylphenols, salts of aryl- or alkyl-aryl-sulfonic acids, salts of ethoxylated benzenesulfonic acids, or soaps.

Suitable dispersing agents are cellulose pitch (salts of sulfite cellulose waste liquor), salts of naphthalenesulfonic acid or, in certain cases, hydrated silicic acids or kieselguhr.

As grinding auxiliaries, suitable inorganic or organic salts, for example sodium sulfate, ammonium sulfate, sodium carbonate and sodium bicarbonate, sodium thiosulfate, sodium stearate, or sodium acetate may be used.

The content of the active substances in the products is generally from 2 to 75% by weight. The active substances may be present in these products also in admixture with other known active substances.

Simple compositions suitable for testing the activity of the components may be obtained in the following manner:

Wettable powder 6 g of active substance are ground with 6 g of finely dispersed silicic acid, and subsequently mixed in a mixer with 48 g of a mixture containing 13.3% of cellulose pitch, 65.4% of quartz and aluminium silicate (Sillitin $2^{(R)}$); 15.3% of finely dispersed silicic acid, 4.7% of polypropylene-glycol and 1.3% of the sodium salt of oleylmethyltauride (Hortapon$^{(R)}$). Thus, 60 g of a 10 % wettable powder are obtained.

Emulsifiable concentrate 2 g of active substance, 16 g of cyclohexanone and 2 g of alkylaryl-polyglycol ether alcohol (Hostapal$^{(R)}$) are mixed with each other. 20 g of a 10 % emulsifiable concentrate are obtained.

The active substances to be used in accordance with the present invention in the veterinary field are applied normally by spraying, dusting or dipping methods, as well as, in the special case of the anti-tick agents, in the so-called dip or spray equipment.

For use as insecticides, acaricides and/or nematocides, the above mentioned formulations of active substances may be diluted to application concentrations of 0.001 weight % of active substance; water being the preferred diluent.

The following Examples illustrate the invention.

General preparation 0.1 Mole of halohomothiochromane of formula II is added, at room temperature and with agitation, to a solution or suspension of 0.10 to 0.11 mole of a sodium salt of a phosphorus compound of formula III ($R_5$ = SNa) in 200 ml of glycol-dimethyl ether. Stirring is continued for about 3 to 5 hours at 50°C, the precipitated salt is separated by suctionfiltration, the filtrate is diluted with about 400 ml of benzene, the organic phase is thoroughly washed with water and dried over $Na_2SO_4$. After having distilled off the solvent, the products of the process are obtained as oils which, in part, crystallize on trituration.

According to the process described above, the following compounds are obtained; the composition of which is confirmed by elementary analysis and which are characterized by refractive index and/or melting point.

TABLE

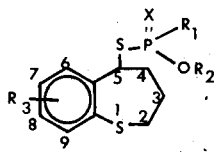

| Example | $R_1$ | $R_2$ | $R_3$ | X | $n_D$ or m.p. (°C) |
|---|---|---|---|---|---|
| 1 | $OCH_3$ | $CH_3$ | H | S | 78–80 |
| 2 | $OC_2H_5$ | $C_2H_5$ | H | O | $n_D^{23.5}$ 1.5663 |
| 3 | $CH_3$ | $C_2H_5$ | H | S | $n_D^{22}$ 1.6151 |
| 4 | $OCH_3$ | $CH_3$ | 7-Cl | S | 70–72 |
| 5 | $OC_2H_5$ | $C_2H_5$ | 7-Cl | S | $n_D^{24}$ 1.6005 |
| 6 | $OC_2H_5$ | $C_2H_5$ | 7-Cl | O | $n_D^{25}$ 1.7581 |
| 7 | $CH_3$ | $CH_3$ | 7-Cl | S | 80–83 |
| 8 | $CH_3$ | $C_2H_5$ | 7-Cl | S | 56–58 |
| 9 | n-$C_4H_9$ | $C_2H_5$ | 7-Cl | S | $n_D^{25}$ 1.6068 |
| 10 | $OC_2H_5$ | $C_2H_5$ | 7-$CH_3$ | S | 53–58 |
| 11 | $OC_2H_5$ | $C_2H_5$ | 7-$C(CH_3)_3$ | S | 58–60 |
| 12 | $OC_2H_5$ | $C_2H_5$ | 7-F | S | 55–57 |
| 13 | $CH_3$ | $CH_3$ | 7-F | S | $n_D^{31}$ 1.621 |

EXAMPLES OF APPLICATION

Example I

Young apple trees planted in pots and heavily infested with a phosphoric ester resistant strain of the European red mite (Metatetranychus ulmi) were sprayed, until drip-off, with the aqueous dilution of an emulsifiable concentrate containing 0.006 weight % of the preparation of Example 5, and subsequently placed in a greenhouse at 20°C.

A microscopic control after 8 days showed that all mobile and immobile stages including the eggs were killed.

Tested in the same manner, the compounds of Examples 2, 3, 7, 8 and 9 proved to be of equal activity.

The following commercial phosphoric acid esters used in comparative tests showed no activity even at considerably higher concentrations:

| | | |
|---|---|---|
| phenkapton | 0.025 weight % of AS*[)] | no effect |
| demeton-S-methyl | 0.05 weight % of AS | no effect |
| dimethoate | 0.05 weight % of AS | no effect |

*[)]active substance

Example II

Bean plants (Phaseolus vulgaris) heavily infested with a phosphoric acid ester resistant spider mite strain (Tetranychus urticae) were sprayed, until drip-off began, with an aqueous dilution of a wettable powder concentrate containing 0.003 weight % of active substance of Example 3. Subsequently, the sprayed plants were placed in a greenhouse at 20°C. Examination under the microscope after 8 days proved that all mobile and immobile stages of the mites including the eggs were killed.

The phosphoric acid esters tested comparatively showed none or only insufficient activity despite high concentration of active substance.

| | |
|---|---|
| diazinone 0.1 weight % of AS | 46 %*[)] killing rate of mite population |
| azinphos-ethyl 0.1 weight % of AS | 63 %*[)] killing rate of mite population |
| dimethoate 0.1 weight % of AS | no effect |
| demeton-S-methyl 0.1 weight % of AS | no effect |

*[)] activity degree according to Abbot

Example III

Horse beans (Vicia faba) heavily infested with bean aphids (Doralis fabae) were sprayed, until beginning drip-off, with the aqueous dilution of an emulsifiable condentrate containing 0.006 weight % of the preparation of Example 2. The sprayed plants were then placed at 20°C in a greenhouse; evaluation was carried out 24 hours after the spraying. All aphids were killed.

Tested in the same manner, the compounds of Examples 3, 5, and 8 showed equal activity.

Example IV

Young cotton plants (Gossypium spec.) in pots, infested with African cotton strainers (Dysdercus fasciatus), were sprayed, until drip-off, with the aqueous dilution of a wettable powder concentrate containing 0.0125 weight % of the active substance of Example 3. Subsequetnly, the plants containing the bugs were put into cylindrical gauze cages and placed in a greenhouse at 20°C. A control after 48 hours showed that all cotton stainers were killed.

Tested in the same manner, the compound of Example 7 showed the same good activity. The phosphoric acid ester azinphos-ethyl tested comparatively showed its activity only at a concentration of 0.05 % of AS.

Example V

Larvae (4th stage) of the Mexican bean beetle (Epilachna varivestis) and leaves of the dwarf-bush bean (Phaseolus vulgaris) were sprayed, by means of a spraying apparatus, with a dosed amount (corresponding to an application amount of 600 liters of spray liquor/ha in the open fields) of the aqueous dilution of an emulsifiable concentrate containing the active substance of Example 2 in a concentration of 0.0024 mg/cm². The leaves and beetle larvae were placed in the laboratory in open vessels at 22°C. The control 48 hours after spraying proved that all larvae were killed.

Tested in the same manner, the compound of Example 8 had equal activity.

Example VI

Larvae (4th stage) of the yellow fever mosquito (*Aedes aegypti*) were placed in beakers containing 100 ml of an aqueous dilution of a wettable powder concentrate of the active substance of Example 5, the concentration being 0.006 ppm. This concentration was sufficient to kill all larvae within 24 hours.

This concentration amounts to only 1/6000 of that killing fishes (*Lebistes reticulatus*) within the same period of time.

Example VII

In vitro test on ticks of the *Boophilus microphus* species

1. *Boophilus microplus* (strain Mexico, normal sensitivity)
2. *Boophilus microplus* (strain Biarra, resistant)

For the preparation of a suitable formulation, 10 parts by weight of active substance were dissolved in 100 parts by volume of a mixture of cyclohexanone and nonylphenol (10 EO, 8:1), and the emulsifiable concentrate so obtained was diluted with water to attain the desired concentration.

10 Adult female ticks of the cited species which had sucked themselves full of blood, were dipped for 5 minutes into these dilutions. Subsequently, the ticks were sticked with their dorsal side onto an adhesive tape and kept in a warming closet (28°C, about 80 % of relative air moisture) for the oviposition.

Two weeks after the treatment, the activity of the formulations was determined by evaluating the inhibition of oviposition, which is expressed in percent; 100 % meaning that all ticks treated with one active substance concentration did not oviposit, 0 % meaning that all ticks did oviposit.

TABLE I

In vitro test on *Boophilus microplus*, strain Mexico (sensitive)

| AS acc. to Example | concentration of AS in % | inhibition of oviposition in % |
|---|---|---|
| 2 | 0.2 | 100 |
|   | 0.05 | 100 |
|   | 0.0125 | 100 |
|   | 0.0031 | 30 |
| 3 | 0.2 | 80 |
|   | 0.05 | 80 |
|   | 0.0125 | 100 |
|   | 0.0031 | 80 |
| 4 | 0.2 | 100 |
|   | 0.05 | 90 |
|   | 0.0125 | 60 |
|   | 0.0031 | 40 |
| 5 | 0.2 | 100 |
|   | 0.05 | 80 |
|   | 0.0125 | 60 |
|   | 0.0031 | 50 |
| 10 | 0.2 | 90 |
|   | 0.05 | 100 |
|   | 0.0125 | 60 |
|   | 0.0031 | 0 |
| 6 | 0.2 | 100 |
|   | 0.05 | 100 |
|   | 0.0125 | 90 |
|   | 0.0031 | 100 |
| 8 | 0.2 | 90 |
|   | 0.05 | 90 |
|   | 0.0125 | 100 |
|   | 0.0031 | 90 |
| 7 | 0.2 | 100 |
|   | 0.05 | 90 |
|   | 0.0125 | 90 |
|   | 0.0031 | 90 |

TABLE II

In vitro test on *Boophilus microplus*, strain Biarra (resistant)

| AS acc. to Example | concentration of AS in % | inhibition of oviposition in % |
|---|---|---|
| 3 | 0.2 | 80 |
|   | 0.05 | 80 |
|   | 0.0125 | 60 |
| 5 | 0.2 | 90 |
|   | 0.05 | 90 |
|   | 0.0125 | 50 |
| 8 | 0.2 | 90 |
|   | 0.05 | 60 |
|   | 0.0125 | 30 |
| 6 | 0.2 | 80 |
|   | 0.05 | 80 |
|   | 0.0125 | 60 |
| 7 | 0.2 | 90 |
|   | 0.05 | 50 |
|   | 0.0125 | 20 |

The generic names cited in the Examples of application stand for the following active substances:

phenkapton = diethyl-S-dichlorophenyl-mercaptomethyl-dithiophosphate demeton-S-methyl = O,O-dimethyl-S-(3-thiapentyl)-monothiophosphate dimethoate = O,O-dimethyl-S-(N-methyl-carbamoylmethyl)-dithiophosphate diazinon = O,O-diethyl-O-(2-isopropyl-4-methyl-6-pyrimidinyl)-thiophosphate azinphos-ethyl = O,O-diethyl-S-(4-oxo-1,2,3-benzotriazin-3-methyl)-dithiophosphate

Example VIII

Systemic activity in animals; model test on guinea pigs

For the preparation of an administrable formulation, the active substances were dissolved in olive oil at a rate of 5% (g/v) and administered as oily solution orally in a dose of 100 mg/kg of body weight to guinea pigs by means of a probang.

Before the treatment, as a comparison, as well as 1, 3, 7 and 24 hours after the treatment, 10 adult, unfed bedbugs (*Cimex lectularius*) each were placed for blood-sucking on the shaved abdominal skin of the guinea pigs.

The mortality rate of the test insect groups fed on the treated guinea pigs was evaluated until up to 24 hours after the absorption of blood. There was a 100 % activity degree when all test insects had been killed after the absorpiton of blood; it was zero, when all test insects of a group were still living.

Test of animal-systemic activity: model test on guinea pigs

| AS acc. to Example | Dose mg/kg | hrs. after treatment placed for blood-sucking | % mortality, hours after blood-sucking | | | |
|---|---|---|---|---|---|---|
| | | | 1 | 2 | 3 | 4 |
| 1 | 100 | comparison | 0 | 0 | 0 | 0 |
|   |     | 3 | 0 | 0 | 0 | 0 |
|   |     | 7 | 100 | | | |
|   |     | 24 | 0 | 0 | 0 | 0 |
| 4 | 100 | comparison | 0 | 0 | 0 | 0 |
|   |     | 3 | 0 | 20 | 70 | 100 |
|   |     | 7 | 100 | | | |
|   |     | 24 | 0 | 0 | 0 | 0 |

What is claimed is:

1. 5-homothiochromanyl-(di)-thio-phosphoric (-phosphonic) acid esters of the formula

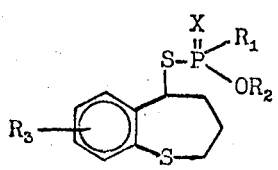

I where
$R_1$ is $(C_1-C_4)$alkyl, $(C_1-C_4)$ alkoxy,
$R_2$ is $(C_1-C_4)$alkyl,
$R_3$ is hydrogen, $(C_1-C_4)$ alkyl or halogen, and
X is oxygen or sulfur.

2. O-ethyl-S-(homothiochroman-5-yl)-methylphosphonodithioate.

3. O,O-diethyl-S-(7-chloro-homothiochroman-5-yl)-phosphorodithioate.

4. O,O-diethyl-S-(7-chloro-homothiochroman-5-yl)-phosphorothioate.

5. O-methyl-S-(7-chloro-homothiochroman-5-yl)-methylphosphonodithioate.

6. O-ethyl-S-(7-chloro-homothiochroman-5-yl)-methylphosphonodithioate.

7. O,O-diethyl-S-(7-fluoro-homothiochroman-5-yl)-phosphorodithioate.

8. O-methyl-S-(7-fluoro-homothiochroman-5-yl)-methylphosphonodithioate.

* * * * *